United States Patent [19]
Eckenhoff

[11] Patent Number: 5,941,844
[45] Date of Patent: Aug. 24, 1999

[54] METHOD AND DEVICE FOR CONTROLLING MAMMALIAN REPRODUCTIVE CYCLE

[75] Inventor: James B. Eckenhoff, deceased, late of Los Altos, Calif., by Bonnie J. Eckenhoff, executor

[73] Assignee: ALZA Corporation, Palo Alto, Calif.

[21] Appl. No.: 08/972,029

[22] Filed: Nov. 17, 1997

[51] Int. Cl.⁶ .................................................... A61N 1/30
[52] U.S. Cl. .............................................................. 604/20
[58] Field of Search ................................... 604/49, 890.1, 604/20, 289; 607/115; 210/502.1, 638; 424/449

[56] References Cited

U.S. PATENT DOCUMENTS

| | | | |
|---|---|---|---|
| 3,860,701 | 1/1975 | Short | 424/81 |
| 4,153,689 | 5/1979 | Hirai et al. | 424/178 |
| 4,800,191 | 1/1989 | Schally et al. | 514/15 |
| 5,013,293 | 5/1991 | Sibalis | 604/20 |
| 5,162,306 | 11/1992 | Donaldson | 514/12 |
| 5,312,325 | 5/1994 | Sibalis | 604/20 |
| 5,372,579 | 12/1994 | Sibalis | 604/20 |
| 5,470,847 | 11/1995 | Garfield et al. | 514/171 |

FOREIGN PATENT DOCUMENTS

WO 93/03790  3/1993  WIPO ............................... A61N 1/30

OTHER PUBLICATIONS

Ainsworth, et al., "Continuous Infusion of Gonadotrophin-releasing Hormone (GnRH) Advances the Onset of Oestrous Cycles in Thoroughbred Mares on Australian Studfarms", J. Reprod. Fert. Suppl. 44 (1991), 235–240.

Turner, J.E., et al., "The Effect of Various Gonadotrophin-releasing Hormone Regimens on Gonadotrophines, Follicular Growth and Ovulation in Deeply Anoestrous Mares", J. Reprod. Fert. Suppl. 44 (1991), 213–225.

The Horse, J. W. Evans, 2nd Ed., Ch. 11, pp. 351–373, W.H. Freeman & Co. (1990) "Anatomy and Physiology of Reproduction in the Mare".

Freeman, et al., Mare Management: Economics necessitate knowledge of reproductive cycle. Large Animal Veterinarian Jul./Aug. 1992, pp. 6–8.

Becker, et al., "Effects of Gonadotropin–Releasing Hormone Infused in a Pulsatile or Continuous Fashion on Serum Gonadotropin Concentrations and Ovulation in the Mare". J. Anim. Sci 1992 70:1208–1215.

Hyland, et al., "Control of Transitional Anestrus in Mares by Infusion of Gonadotropin in Releasing Hormone". Theriogeneology, Jun. 1988, vol. 29, No. 6, pp. 1383–1391.

Lowis, et al., "The Effect of an Extended Artificial Photoperiod and Gonadotrophin–releasing Hormone Infusions in Inducing Fertile Oestrus in Anoestrous Mares". Australian Veterinary Journal, vol. 68, No. 12, Dec. 1991, pp. 400–402.

Hyland, et al., "Infusion of Gonadotrophin–releasing Hormone (GnRH) Induces Ovulation and Fertile Oestrus in Mares During Seasonal Anoestrus". J. Reprod. Fert. Suppl. 35 (1987), pp. 211–220.

Meinert, et al., "Advancing the Time of Ovulation in the Mare with a Short–term Implant Releasing the GnRH Analogue Deslorelin". Equine Veterinary Journal (1993), 25 (1) pp. 65–68.

(List continued on next page.)

Primary Examiner—Manuel Mendez
Attorney, Agent, or Firm—D. Byron Miller; Steven F. Stone

[57] ABSTRACT

A method encompasses the substantially continuous electrotransport delivery of luteinizing hormone releasing hormone (LHRH), prologues, analogues, salts or mixtures thereof, preferably at a substantially constant rate, to a female mammal for the purpose of modifying its reproductive cycle. An electrotransport device substantially is suited for the continuous delivery of LHRH prologues, analogues, salts or mixtures thereof over an extended period of time to a mammal. The present technology may be successfully applied to the controlled breeding of mammals, such as thoroughbred race horses.

19 Claims, 6 Drawing Sheets

OTHER PUBLICATIONS

McKinnon, et al., "Short Communications: Predictable Ovulation in Mares Treated with an Implant of the GnRH Analogue Deslorelin", Equine Veterinary Journal (1993) 25 (4) pp. 321–323.

Kesler, D.J., et al., "Constant Delivery of GnRH to Infertile or Subfertile Females with Hypothalamic–Pituitary Axes that Release Hormones in Episodic Bursts". Proceed. Intern. Symp. Control. Rel. Bioact. Mater. 14 (1987), Controlled Release Society, Inc.

Lu, M. Fu, et al., "The Effects of Formulation Variable on Iontophoretic Transdermal Delivery of leuprolide to Humans", Drug Development and Industrial Pharmacy, 19(13), pp. 1557–1571 (1993).

Heit, Mark C., et al., "Transdermal Iontophoretic Peptide Delivery: In Vitro and In Vivo Studies with Luteinizing Hormone Releasing Hormone". Journal of Pharmaceutical Sciences, vol. 82, No. 3, Mar. 1993 pp. 240–243.

Kumar, Saran, et al., "Effect of Iontophoresis o in Vitro Skin Permeation of an Analogue of Growth Hormone Releasing Factor in the Hairless Guinea Pig Model". Journal of Pharmacutical Sciences, vol. 81, No. 7, Jul. 1992, pp. 635–639.

Kumar, Saran, et al., "In Vivo Transdermal Iontophoretic Delivery of Growth Hormone Releasing Factor GRF (1–44) in Hairless Guinea Pigs". Journal of Controlled Release, 18 (1992) 213–220.

Chen, et al., Pharmaceutical Research vol. 9, No. 10, Oct. 1992 (Supplement), BIOTEC 2023, "Ionotophoretic Transdermal Delivery of LHrh: (II) Effect of electrical Parameters".

Kumar, Krishna, et al., Pharmaceutical Research Vo. 9, No. 10, Oct. 1992 (Supplemental) BIOTEC 2024, "Iontophoretic Transdermal Delivery of a Decapeptide".

Merck Index, pp. 859–860 and 711.

Merck Index, pp. 862–863, 583, 669 and 1234.

METHOD AND DEVICE FOR CONTROLLING MAMMALIAN REPRODUCTIVE CYCLE

TECHNICAL FIELD

This invention relates to the controlled delivery of leutinizing hormone releasing hormone (LHRH) or an analog of LHRH by electrotransport to female animals, particularly female breeding animals, to control ovulation. More particularly, this invention relates to the transdermal electrotransport delivery of LHRH or an analog thereof to mares to control the time of birth of a colt.

BACKGROUND ART

The ability to control an animal's date of birth is generally of importance in animal breeding. More particularly, the economic considerations surrounding the breeding of some species, e.g., thoroughbred race horses, have traditionally inspired creative scientific approaches to equine breeding. The ability to accurately and precisely select equine birth dates is especially important in light of the official determination, by the breeder's association, of January 1 as the universal birth date of thoroughbred horses for racing purposes. That is, all horses born within a calendar year are presumed to have a January 1 birth date for racing purposes. Thus, animals born earlier within any given calendar year have a significant developmental advantage over those born later in the same year. Accordingly, substantial research and development efforts have been directed at controlling the equine reproductive cycle in order to produce horses with actual birth dates on or shortly after January 1 and, thereby, augment the developmental state of thoroughbred horses.

Female horses experience estrous cycles about 21–23 days in length, with some seasonal variations, except for a period of about two to five months. During the latter period, the mare typically experiences an anestrous period, i.e. a period of sexual inactivity. This period commonly ranges in the northern hemisphere from about November to March (see, for example, The Horse, J. W. Evans, 2nd Ed., pp. 351–373, W. H. Freeman & Co. (1990)). However, since the gestation period of the mare is about 335–340 days, February is the ideal month for mare impregnation in order to achieve an early birth date in the following calendar year, i.e. in January or February. Since in the northern hemisphere mares typically go through their yearly anestrous period during these months, the onset of estrous to attain an early birth date must be induced artificially.

In the northern hemisphere, the largest number of mares experience ovulation during the longest daylight periods of June. The observation of this correlation between extended daylight periods and increased mare ovulation rates led to the management of equine breeding by "extending the photoperiod". Thus, ovulation has been induced during the anestrous period by placing mares under artificial lighting to, thereby, extend the perceived daylight period up to about 16 hours per day.

Both follicular development and the onset of ovulation are dependent on the presence of certain hormones, such as luteinizing hormone (LH), follicle-stimulating hormone (FSH), estrogen, and progesterone (see, for example, D. Freeman et al., "Mare management", Large Animal Vet.: 6–8 (July/August, 1992)). The blood levels of these hormones vary in a relatively predictable manner during the normal female equine reproductive cycle. Ovulation has also been induced in a mare by delivery of pharmaceuticals which interfere with the hormonal cycle of the mare. Prostaglandin and its analogues, for example, have been delivered to mares to cause the regression of the corpus luteum, and to thereby attain a reduction of the estrous period. Progesterone has also been delivered to either suppress or synchronize the heat periods in mares having long and erratic estrous cycles.

LHRH (also known as gonadotropin releasing hormone or GnRH) and follicle-stimulating hormone (FSH) have been employed to alter the female equine reproductive cycle. LHRH has been delivered to equines by various methods, including injection and implantation. For instance, LHRH has been delivered by intravenous and intramuscular injection in order to determine its effect on the release of luteinizing hormone (LH) and ovulation (see, J. E. Turner, "The Effect of Various Gonadotropin-releasing Hormone Regimes on Gonadotrophins, Follicular Growth and Ovulation in Deeply Anoestrous Mares", J. Reprod. Fert. Suppl. 44:213–225 (1991)). LHRH has also been successfully delivered to mares from subcutaneously implanted osmotic minipumps, which are commercially available from ALZA Corporation, Palo Alto, Calif.) to induce ovulation (see, C. G. V., Ainsworth, "Continuous Infusion of Gonadotropin-releasing Hormone (GnRH) Advances the Onset of Oestrous Cycles in Thoroughbred Mares on Australian Stud Farms", J. Reprod. Fert, Suppl 44:235–240 (1991)).

Although some induction of ovulation was attained in mares by injection and implantation of LHRH and its analogs, there are drawbacks associated with these delivery techniques. One important problem associated with injections is the pulsatile nature of the delivery, which typically cannot provide the desired uniformity of drug concentration in the bloodstream. Another problem with injecting LHRH is its short half life, requiring frequent injections to maintain LHRH plasma levels. Another problem associated with this, and other non-continuous delivery systems, is that they require repeated human intervention by highly trained personnel to administer injections on a regular basis. On the other hand, implantation techniques have unique problems associated with the surgical procedure required for the subcutaneous insertion of the device. These problems require sterilization to prevent infections, which increase labor costs, and produce significant mare discomfort, which may cause rubbing or scratching at the implantation site.

As used herein, the term "electrotransport", refers generally to the passage of a substance through a body surface, such as skin, mucous membrane, or nails, induced at least partially by an electrical field. For example, a therapeutic agent may be introduced into an animal's body by one of several electrotransport processes. One form of electrotransport, called iontophoresis, involves the electrically induced transport of charged ions. Another type of electrotransport, electroosmosis, involves the movement of a liquid and all agents, including uncharged agents, dissolved therein under the influence of an electric field. Still another type of electrotransport, electroporation, involves the transport of an agent through transiently-existing pores formed in the skin or other biological membranes by the application of an electric field. In any given electrotransport process, however, more than one of these processes may be occurring simultaneously to some extent. Accordingly, the term "electrotransport" is used herein in its broadest possible meaning, which includes the electrically induced or enhanced transport of at least one agent, which may be charged, or uncharged, or mixtures thereof, regardless of the specific mechanism or mechanisms by which the agent is actually transported.

Sibalis U.S. Pat. Nos. 5,013,293; 5,312,325 and 5,372,579 all disclose an electrolytic transdermal patch provided with a current oscillator for the periodic delivery of LHRH to induce or inhibit ovulation. The patent teaches delivering "pulses" of electrotransport current, each pulse being about 6 minutes in duration, at a frequency of one 6 minute pulse per hour, to deliver LHRH to women in order to match the body's natural release of LHRH and thereby induce ovulation. However, the delivery of LHRH at a frequency of two or more 6 minute pulses per hour is said to completely extinguish gonadotrophic secretion and inhibit ovulation (see, column 2, lines 44–57 and column 6, lines 16–30 of Sibalis U.S. Pat. No. 5,013,293).

There is still a need for an effective method of non-invasively delivering LHRH, or an analog thereof, to successfully attain scheduled ovulation, insemination and/or pregnancy, particularly for breeding animals (e.g., cattle and horses) and more particularly for breeding animals having seasonal anestrous periods.

DESCRIPTION OF THE INVENTION

This invention provides a method of controlling the estrous cycle, inducing ovulation during an anestrous period, and/or restarting the estrous cycle of a female mammal which is already experiencing some stage of the estrous cycle. This is attained by non-invasively and continuously delivering LHRH, or an analog thereof, to female mammals by transdermal electrotransport. In one embodiment of the invention, a substantially constant electrical potential is applied to deliver the LHRH across a body surface of the mammal. This electrical potential induces or enhances the transport of the LHRH through the body surface, preferably in a substantially continuous manner, and more preferably at a substantially constant rate.

The present invention can be used in the breeding of animals such as cattle and horses. For example, the invention may be used to ensure that one or more female breeding animals (e.g., an entire herd) are ovulating at the same time so that the animals can be inseminated (i.e., by artificial insemination) at the same time, thereby making the use of insemination materials and the scheduling of veterinary visits more efficient. The invention has particular utility in controlling the ovulation of female thoroughbred race horses. In one preferred embodiment, the hormone is continuously delivered by transdermal electrotransport to a female equine (mare) to induce ovulation at a time when the mare is normally in a seasonal anestrous period, after which the mare is naturally or artificially inseminated to achieve impregnation at a seasonal time which results in the colt being born soon after January 1. In another preferred embodiment, the hormone is continuously delivered by transdermal electrotransport to female breeding animals (e.g., cattle, sheep, pigs, etc) to induce ovulation at a time when the animal is normally in a seasonal anestrous period, after which the animals (e.g., an entire head) are artificially inseminated to achieve impregnation.

MODES FOR CARRYING OUT THE INVENTION

The term "LHRH", as used herein, includes all the natural and synthetic analogs and prodrugs (e.g., esters) of LHRH, including LHRH and salts of LHRH, such as, gonadorelin acetate, e.g. LUTREPULSE (sold by Ortho Pharmaceuticals, Raritan, N.J.); Cystorelin (sold by Abbott Laboratories, N. Chicago, Ill.); Hypocrine (sold by Tanabe Seiyaku Co., Ltd., Osaka, Japan); Lutrelef (sold by Ferring AB, Malmo, Sweden); LHRH acetate (e.g., Ovarelin); LHRH hydrochloride (e.g. Factrel, sold by Wyeth-Ayerst, New York, N.Y.); Goserelin and its salts (e.g., Zoladex, sold by Zeneca Pharmaceuticals, London, UK); Leuprolide and its salts (e.g., Carcinil and Lucrin, both sold by Abbott Laboratories); Lupron (sold by TAB, N. Chicago, Ill.; gonadotropin-releasing factor; gonadotropin-releasing hormone (GnRH); prodrugs thereof, analogs thereof, salts thereof, and mixtures thereof, among others. Of these, water soluble salts of LHRH and anologs of LHRH are most preferred.

The present invention provides for the non-invasive electrotransport delivery through a body surface (e.g., skin of an animal) of LHRH in a substantially continuous manner in order to induce ovulation. The LHRH is preferably delivered in a substantially continuous manner, and more preferably at a substantially continuous rate, over a period of time effective to induce ovulation.

This invention, therefore, generally relates to a method of modulating the reproductive cycle of a female mammal by electrotransport administration, through a body surface of the mammal, of a composition comprising LHRH, in a substantially continuous manner, preferably at a substantially constant rate. In one preferred embodiment, the LHRH is administered over a period of time effective to induce ovulation. The continuous administration of LHRH to a mammal in an estrous cycle over a predetermined number of days restarts ovulation without inhibiting the estrous cycle, as occurred with the pulsatile method of the prior art.

The LHRH is preferably continuously delivered by electrotransport for at least about 80%, preferably for at least about 90%, and more preferably for at least about 95% of the administration period. In some cases, the LHRH may be administered for about 98 to 99%, and even up to about 100% of the administration period. The electrotransport delivery of LHRH generally produces increased secretion of luteinizing hormone (LH) and a corresponding increase in serum LH concentration within about 5 to 10 days after starting the administration. The administration of the LHRH may be commenced during an estrous period to restart the estrous cycle at a predetermined time, generally about 3 to 7 days after commencement of delivery. The administration of the agent may also be started within an anestrous cycle to start the estrous cycle at a predetermined time, generally about 3 to 7 days thereafter. The rate of LHRH delivery remains, preferably, substantially constant over the administration period. This means that the amount of LHRH delivered through the body surface in any given unit of time, e.g., 1 hour, remains within about 30%, more preferably within about 20%, and still more preferably within about 10%, of the amount delivered in any other unit of time within the administration period. In some cases, the amount per unit time of LHRH delivered may even remain within about 5%, and even about 3 to 2% within the administration time period.

Figure 2:
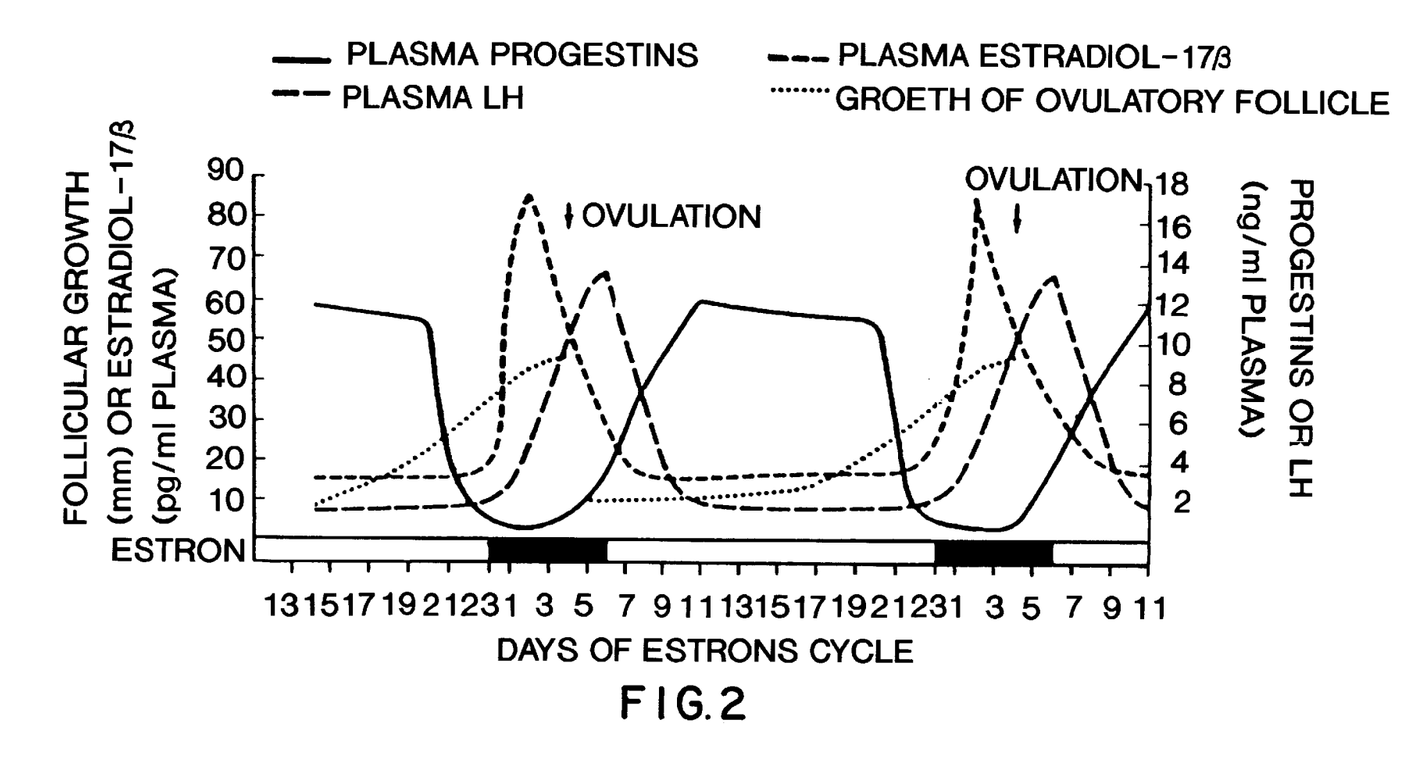
FIG. 2 is a graph showing typical concentrations of selected hormones in the blood serum of a horse as a function of time during the horse's estrous cycle.

Another preferred embodiment of the method utilizes a substantially constant applied electric current. Since in this case, the electric current is applied substantially continuously, the delivery of LHRH through the selected body surface is assumed to occur substantially continuously, i.e., over at least about 80%, preferably at least about 90%, and more preferably at least about 95% of the administration period. In some cases, the current may even be applied substantially continuously at least about 98–99%, and even up to 100% of the delivery time. Thus, the agent is delivered in a substantially continuous manner and not as a pulse over a short period of time with long periods of time in-between, during which time no delivery is attained. In a most preferred embodiment, LHRH is delivered substantially without interruption during the entire extended delivery period. A preferred rate of delivery of the agent is about 0.01 to 10 mg, and more preferably about 0.05 to 5 mg, over a period of about 1 to 10 days, or 500 $\mu$g/day to 10 mg/day, preferably 1 mg/day to mg/day and more preferably about 1 mg/day to 5 mg/day. The administration of LHRH induces a first initial surge in the serum concentration of luteinizing hormone (LH) and a subsequent increase in follicle stimulating hormone (FSH), progesterone, and estradiol over the following 20 days, all of which are consistent with the induction of ovulation (see, FIG. 2). In another embodiment of the method of this invention, when the electrotransport administration of the LHRH is stopped, a second surge in LH serum concentration is attained, which is indicative of the initiation of an estrous cycle.

The method of this invention may be custom tailored to obtain any specific birth date, within some margin of error, by calculating back the starting date and period of delivery of LHRH. This may be done taking into consideration the desired birth date, the gestation period of the mammal, and the LHRH delivery period, generally about 1 to 10 days.

In one preferred embodiment, the present invention is applied to the breeding of horses, by administering LHRH to female equines for the improved breeding of horses, such as thoroughbred race horses. This method is applied to preferably obtain birth dates as close, and subsequent, to January 1 of the following year as possible. Thus, the preferred starting date and period of time for the electrotransport delivery of LHRH to thoroughbred mares are dependent on, and may be calculated, the desired birth date, preferably being as early as January 1, but not before this date, the gestation period of the mare being usually about 335 to 340 days, and the period from initiation of the electrotransport delivery of LHRH to the optimal time for attempting insemination generally being about 5 to 20 days. Considering these factors, the continuous transdermal administration of the LHRH by electrotransport to mares for breeding thoroughbred horses may preferably occur from about, but not before, January 1 to March 30, more preferably from about January 5 to February 15, and most preferably from about January 15 to February 1.

The transdermal administration of LHRH by electrotransport may also be used to select a desired insemination date. In this embodiment of the invention, LHRH is electrotransported through a body surface of the mammal, e.g., the mare, while it experiences some stage of the estrous cycle. This procedure, restarts the estrous cycle of the mare, and is generally undertaken by substantially continuously delivering LHRH by electrotransport for a period of about 0.5 to 10 days, preferably about 1 to 7 days, and more preferably about 2 to 5 days. Over this period of time, the agent is generally delivered at a rate of about 0.05 to 15 micrograms per hour ($\mu$g/hr), preferably about 1 to 10 $\mu$g/hr, and more preferably about 5 to 8 $\mu$g/hr. However, the period and the rate of delivery of LHRH may be varied depending on a number of factors, including the weight of the mammal, e.g., the mare, and its reproductive stage at the time the treatment is started. Regardless of the stage of the estrous cycle, the electrotransport delivery of LHRH to the mammal for the described period of time at the described delivery rate causes the cycle to be started again. Thus, a mammal's cycle may be essentially reset or restarted at any given time by the initiation of electrotransport delivery of LHRH. In this manner, a date may be selected for its insemination by either artificial or natural means, and the initiation time of transdermal electrotransport of LHRH may be calculated based on the knowledge of the time from the initiation of the estrous cycle to the optimal time for insemination, typically about 5 to 20 days, and the time from initiation of LHRH electrotransport to the resetting of the estrous cycle, or about 3 to 7 days. For example, assuming that a male mammal, e.g., a stud, will be available on or about June 24, the optimal time to begin the electrotransport delivery of LHRH to the mare would be about June 10 to June 18. However, in some cases, the period may extend beyond these dates.

Accordingly, the teachings of this invention enable a superior method for controlled breeding of race horses. Generally, this controlled method of breeding entails first delivering LHRH by transdermal electrotransport to a mammal, such as a mare, over a predetermined period of time in a substantially continuous manner, and preferably at a substantially constant rate effective to induce ovulation. A predetermined period of time is then allowed to pass from a date, which is a function of the dates of initiation or cessation of transdermal electrotransport, or both. In one embodiment, this predetermined period may be about 3 to 7 days after initiation of electrotransport delivery. In another embodiment, the period may be within about 2 days of cessation of LHRH electrotransport delivery. During this period subsequent to the cessation of LHRH administration, an endogenous second surge of serum LH concentration generally occurs, which signals the initiation of a newly induced estrous cycle, from which the date of ovulation may be calculated as is known in the art. The mare may be subsequently inseminated, either naturally or artificially, at a time expected to be most likely to achieve impregnation, time which dearly overlaps with the ovulation date, as is known in the art.

Figure 1:
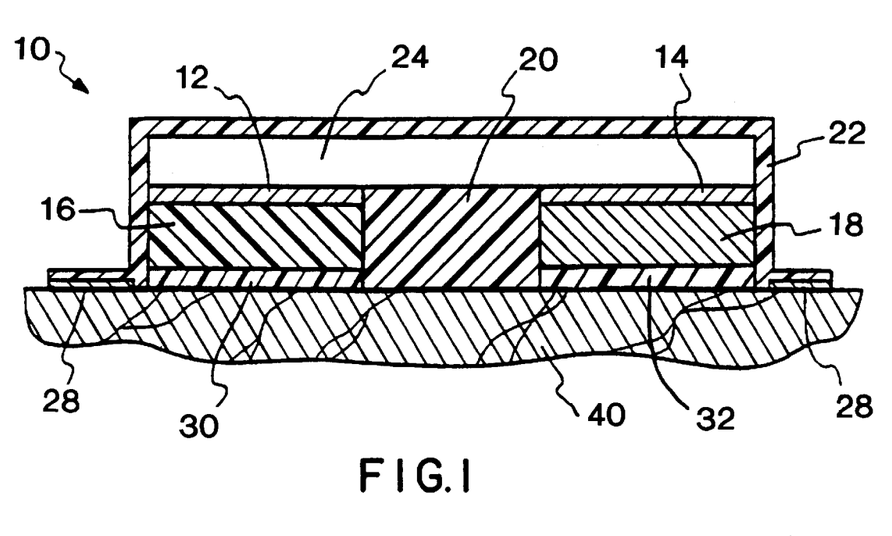
FIG. 1 is a sectional view of one embodiment of a transdermal electrotransport device useful in accordance with the present invention.

The delivery of LHRH according to the present invention may be accomplished by a number of electrotransport devices. One example of an electrotransport device useful for the practice of the present invention is illustrated in FIG. 1. Device 10 has two current distributing members or electrodes, comprised of electrically conductive materials, referred to herein as a donor electrode 12 and a counter electrode 14. The electrodes may be composed of any materials which are sufficiently electrically conductive including, without limitation thereto, silver, silver chloride, zinc, carbon, platinum, and stainless steel. The electrodes may be provided in a variety of forms including metal foil, screen, coatings or polymer/metal composites. The composites may be formed by numerous processes such as extrusion, calendering, film evaporation, or spray coating. In FIG. 1, the donor and counter electrodes 12 and 14 are positioned adjacent to, and in electrical contact with, the donor reservoir 16 and the counter reservoir 18, respectively. The donor reservoir 16 contains the LHRH to be delivered, preferably in the form of an aqueous solution of a water soluble salt of LHRH. The counter reservoir 18 may contain a biocompatible electrolytic salt such as sodium chloride or another agent to be delivered. The reservoirs are formed of any material adapted to absorb and hold a sufficient quantity of liquid therein in order to permit transport of LHRH/ electrolyte therethrough by electrotransport. Preferably, the reservoirs 16 and 18 are formed of one or more hydrophilic polymers such as polyvinylpyrrolidone, polyvinyl alcohol, and/or polyethylene glycols and optionally also contain one or more hydrophobic polymers such as polyisobutylene, polyethylene, or polypropylene. An electrical insulator 20 is positioned between (i) the donor electrode 12 and donor reservoir 16 and (ii) the counter electrode 14 and counter reservoir 18. Insulator 20, which may be an air gap or may be composed of a material which conducts neither electrons nor ions to a substantial extent, prevents device 10 from short-circuiting through a path which does not include the body surface 40 to which the device 10 is applied. The device 10 optionally includes a backing layer 22 composed of a liquid impermeable non-conducting material.

Device 10 has an electronic circuit, illustrated schematically in FIG. 1 as layer 24, having therein a power source, preferably a DC source, e.g., one or more batteries. Typically, the electronic circuit layer 24 may be comprised of electronically conductive pathways printed, painted or otherwise deposited on a thin, flexible substrate such as, for example, a film or polymeric web, e.g. the electronic circuit layer 24 is a flexible printed circuit. In addition to the power source, the electronic circuit layer 24 may also include one or more electronic components which control the level, wave form shape, polarity, timing, etc., of the electric current applied by device 10. For example, the circuit layer 24 may contain one or more of the following electronic components: control circuitry such as a current controller, e.g. a resistor or a transistor-based current control circuit, an on/off switch, and/or a microprocessor adapted to control the current output of the power source over time. The outputs of the circuit layer 24 are electrically connected to the electrodes 12 and 14 such that each electrode is in electrical contact with an opposite pole of the power source within the circuit layer 24.

The device adheres to the body surface in this embodiment by means of a peripheral adhesive layer 28. Optionally, the device may contain an in-line adhesive layer, i.e. an adhesive layer positioned between reservoir 16 and/or 18 and the body surface of the patient. An in-line adhesive must be composed of an ion-transmitting material, i.e. LHRH must be capable of penetrating the adhesive layer to reach the body surface. Optional flux control membranes 30 and 32 are positioned between the donor reservoir 16 and the body surface 40 and between the counter reservoir 18 and the body surface 40, respectively, in order to limit or control the amount of passive, i.e. not electrically assisted, flux of LHRH to the body surface 40.

The device 10 of FIG. 1 is merely one example of an electrotransport device useful in accordance with present invention. In addition, the system may contain other features, such as a removable protective liner (not shown) on the body surface contacting face 32 of the device. Furthermore, certain components in the device 10 are unnecessary or optional according to the present invention. The counter reservoir 18, the passive flux control membranes 30 and 32, and the peripheral adhesive 28 are all examples of optional components. If the materials of electrodes 12 and 14 form a galvanic couple, the independent power source in layer 24 may also become an optional component. Thus, the device 10 of FIG. 1 is presented solely for illustration of one embodiment of the present invention.

LHRH may be electrotransported through many locations, or body surfaces, on a mammal, such as an equine. For example, an electrotransport device may be affixed to the underside of an animal between the front and hind legs. Alternatively, a device may be located on the interior of a leg, preferably a hind leg because of the larger surface area. Both the interior leg and underside locations are difficult for an animal, such as a horse, to reach. However, the delivery of LHRH from an electrotransport device is preferably accomplished through an area of the neck of the mammal, which is preferred because it is very difficult for the animal to bite, scratch with its legs, or swat with its tail. In addition, the application of an electrotransport device to the neck of a mammal is safer and more convenient for the preparation of the application site, i.e. shaving an area of the horse's neck so that the device may be applied directly to the skin.

Preferably, when the agent is administered to a mammal, such as a female equine, an area of the underside located between the front and back legs may be utilized, the area is shaven, and an electrotransport device is applied thereto. In other cases, the agent may be administered through an area of the neck of the mammal, which also requires shaving prior to application of the device.

Prior to applying the device, the selected body surface may be advantageously treated or otherwise prepared to be most suitable for enhancing the delivery rate of the agent. For example, known electrotransport permeation enhancers, such as alcohols, may be utilized in practicing the invention described herein. In the case of delivery of LHRH to an animal such as a mare, the animal's hair is preferably removed from the selected body surface, e.g. by shaving. Hair removal allows the electrodes of the device to be placed in better ion transmitting relation with the skin surface (e.g., skin) and also better permits the device to be adhered to the body surface (e.g., skin).

Having thus generally described the invention, and certain preferred embodiments thereof, the invention will be further illustrated with reference to the following examples.

EXAMPLE 1

Electrotransport Delivery of LHRH to Anestrous Mares

A veterinary clinical study was conducted on mares in Ireland (northern hemisphere) during late October. In the study, electrotransport LHRH delivery devices were applied to a group of three mares, ages 4 to 7 years. LHRH was delivered to the mares by electrotransport in a continuous manner over a 3 day (72 hour) period.

The mares were prepped on the inner thigh of the hind leg with #20 clipper blade and wiped down with isopropyl alcohol. An active, 2 $cm^2$ electrotransport-LHRH patch was applied to each mare on Day 1 of the study. The patches delivered LHRH for 24 hours. New sites were prepped each day of application and a new patch was applied to each mare throughout the three day wearing period. Spent patches, from each 24 hours of wearing, were stripped following application of the new patch. Blood samples were drawn at 24 hours prior to the start of LHRH delivery, and at 0, 0.5, 1.5, 3, 4.5, 6, 8, and 24 hours of treatment for each day of application through the three days of LHRH delivery. Twenty-four hour blood samples were then drawn on Days 4, 5, 6, and 7. Blood samples were then drawn at 0, 0.5, 1.5, 3, 4.5, and 6 hours of Day 21 of the study to conclude the study.

Figure 3:
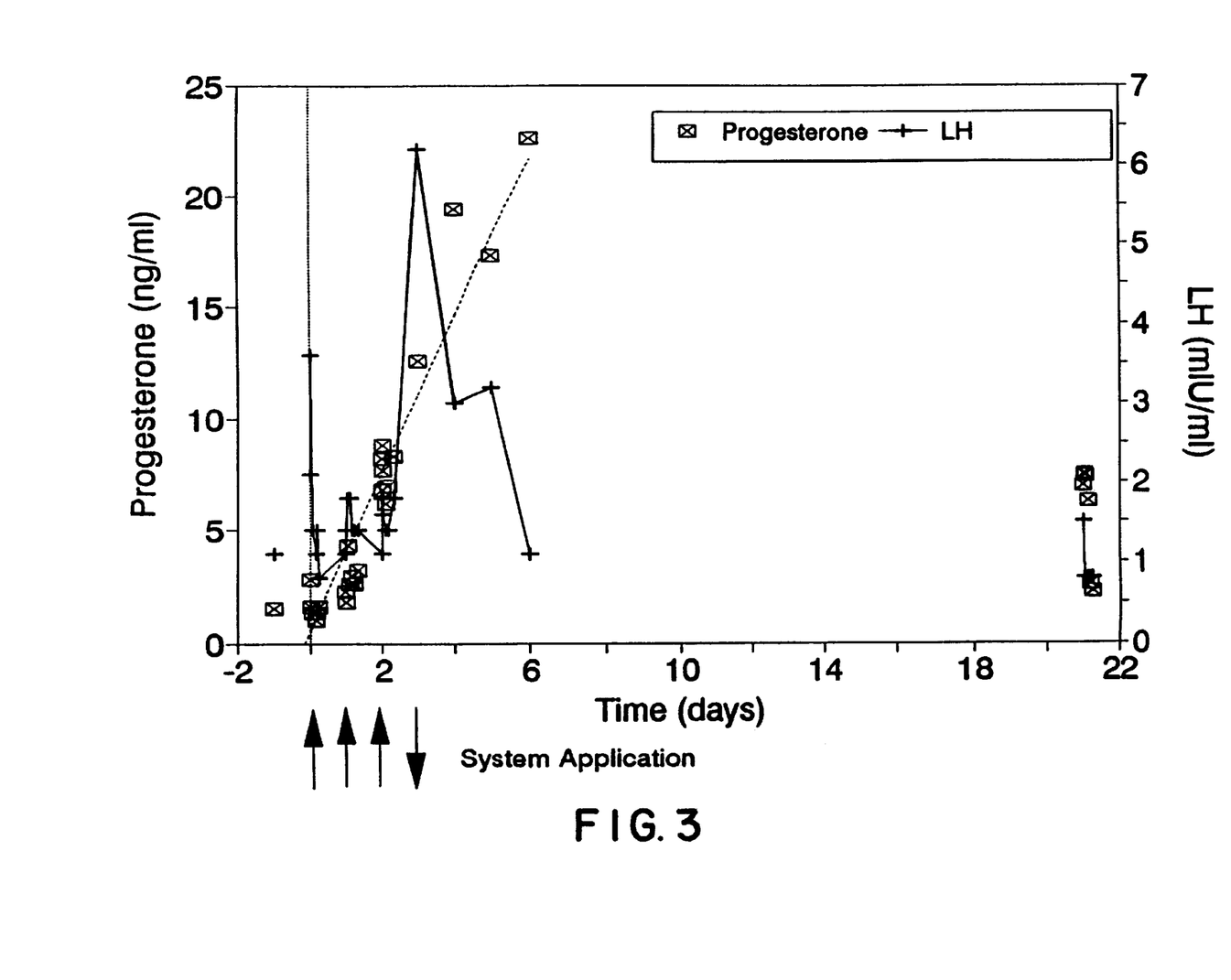
FIG. 3 is a graph showing blood progesterone and luteinizing hormone (LH) levels in a mare participating in a clinical study described in Example 1.
Figure 4:
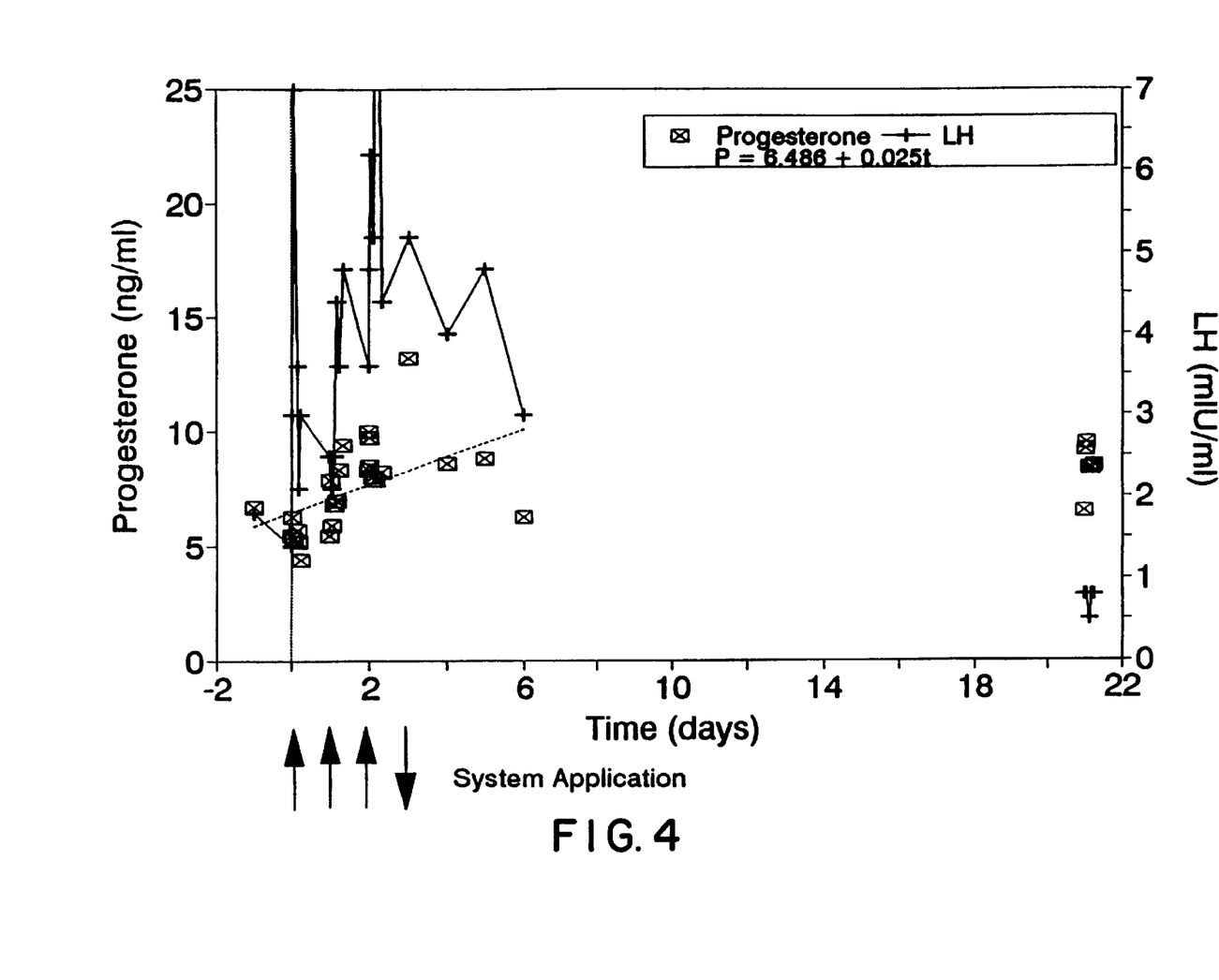
FIG. 4 is a graph showing blood progesterone and luteinizing hormone (LH) levels in another mare participating in the clinical study described in Example 1.
Figure 5:
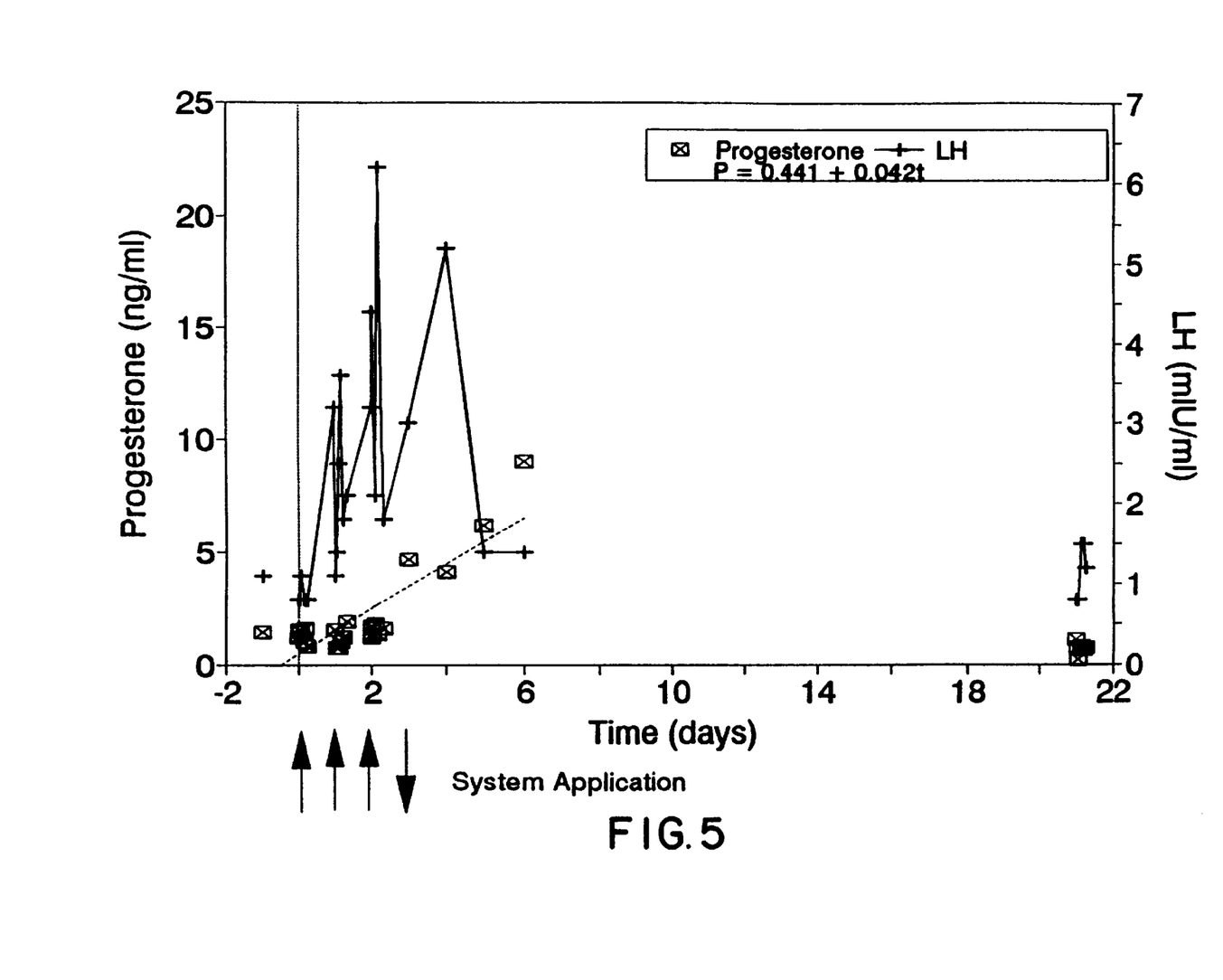
FIG. 5 is a graph showing blood progesterone and luteinizing hormone (LH) levels in yet another mare participating in the clinical study described in Example 1.

Two of the three mares, mares A and C, wore the patches for two sequential 24-hour periods. Mare B wore the patch for only one 24-hour period. FIGS. 3, 4, and 5 show progesterone and LH plasma concentrations of the three mares during the pretreatment, treatment and washout phases.

The plasma concentrations of progesterone (mg/mL) showed a distinct increase on Day 3 of treatment in mare A and were elevated on Days 4 through 7 in mares A and C. In mare B, progesterone concentrations were consistent during the seven days of the feasibility study and on Day 21. The plasma concentrations of luteinizing hormone (mIU/mL) were increased above the normal range throughout the period of treatment (Days 1 through 7) in mare B, and on Days 2 through 6 in mares A and C. The increased concentrations of LH were most consistent on Days 4, 5, and 6 (except in mare C). On Day 21, plasma luteinizing hormone concentrations were generally <1.0 mIU/mL. Increased concentrations refer to concentrations >1.5 mIU/mL.

Mares A and C showed the signs of coming into season. These two mares stood for the teaser stallion on Day 6; whereas, mare B did not show this behavior. These physiological observations are consistent with the blood results obtained in the study for mares A and C which wore the patches for two sequential 24 hour periods.

EXAMPLE 2

Electrotransport Delivery of LHRH to Mares

A veterinary clinical study was conducted on twelve mares in Ireland over a twenty-one day period beginning on April 21st. Since mares in Ireland wouldnaturally be coming out of anestrous during this time frame, the results of this study may not be probative of the effectiveness of treansdermal electrotransport LHRH delivery for starting the estrous cycles of anestrous mares. Nevertheless, the study does show the effectiveness of the devices and clinical methods used in the study for transdermally delivering LHRH into the blood of breeding mares.

Figure 6:
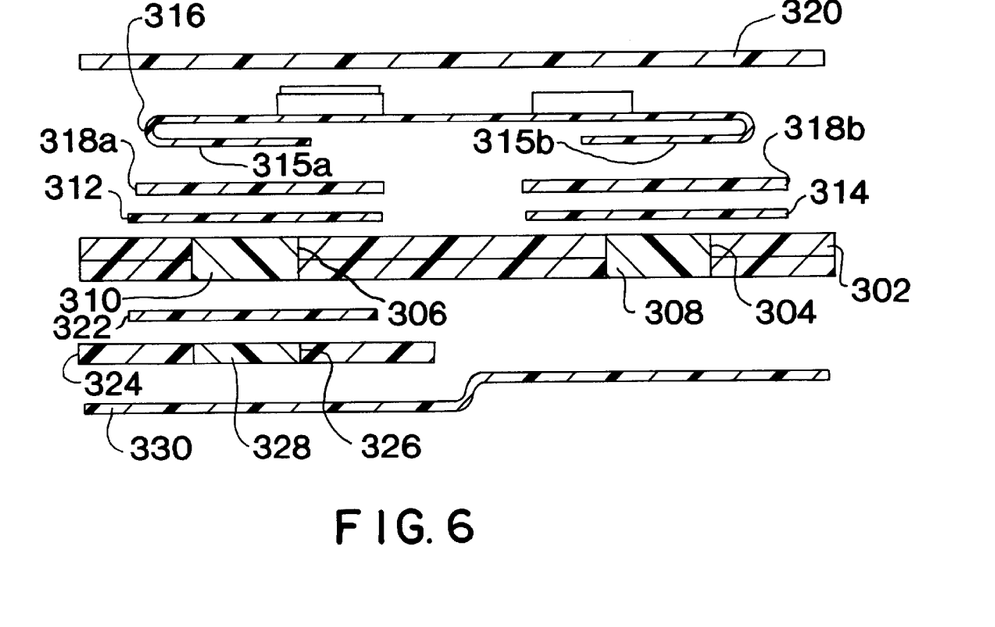
FIG. 6 is a cross sectional view of the electrotransport delivery device used in the in vivo studies of Example 2 herein.

Thirty electrotransport delivery devices were produced having the construction illustrated, in exploded view, in FIG. 6, fifteen of the devices having a 1 $cm^2$ area and 15 having a 2 $cm^2$ area. The current density used was 0.1 $mA/cm^2$, and the total current for the 1 $cm^2$ device was a 0.1 mA while the total current for the 2 $cm^2$ device was 0.2 mA.

Double sided adhesive foam tape having a thickness of 0.8 mm (1/32 in.) was folded over on itself to create a foam layer 302 having a thickness of 1.6 mm (1/16 in.). Then, by use of a NAFE punch press, openings 304,306 were punched out with the die. Gel reservoirs 308,310 containing saline were inserted into the openings 304,306.

A silver foil anodic electrode 312 was placed over the gel 310 and a silver chloride-loaded ethylene vinyl acetate film electrode 314 was placed over gel 308. The electrodes 312,314 were electrically connected to the outputs 315a, 315b of a printed circuit board assembly 316 by means of electrically conductive adhesive strips 318a, 318b (Arclad 8001, Adhesives Research, Allentown, Pa.), respectively. The top of the circuit board assembly 316 was Medpar pigmented film 320 (3M Company, St. Paul, Minn.). The skin side of gel 310 was covered with an anion exchange membrane 322 (Sybron MA 3475, The Electrosynthesis Co., E. Amherst, N.Y.) which is impermeable to cations. A layer 324 of single sided adhesive foam had an opening 326 punched out using the punch press. A LHRH-containing gel reservoir 328 was inserted into the opening 326. The openings 310 and 326 had the same cross-sectional size and shape so they were aligned on top of one another, with the anion exchange membrane 322 sandwiched therebetween. A 0.03 mm (1 mil) thick silicone coated polyester release liner 330 was placed over the skin-contacting surfaces of the device until use.

The circuit board assembly applied an electrotransport currents of 0.1 mA or 0.2 mA, depending upon the cross-sectional areas of gels 308,310 and 328. For those devices having gels with a cross-sectional area of 2 $cm^2$, the applied current was 0.2 mA. For those devices having gels with a cross-sectional area of 1 $cm^2$, the applied current was 0.1 mA. Thus, the applied current density was 0.1 $mA/cm^2$ for all systems.

A blood sample was taken from each mare 24 hours prior to application of the device to establish a pretreatment baseline. During the 5 day application period, blood samples were taken daily at 2 hrs, 6 hrs, and 24 hrs, from the time of initial application of the device.

Subsequent to the removal of the device, blood samples were collected once daily for 15 days until day 20 from the date of the initial application of the device. Lithium heparin was added to the blood samples which were centrifuged to separate out the blood plasma fractions which were stored at $-20°$ C. until assayed.

All plasma samples were analyzed for progesterone, luteinizing hormone (LH), follicle-stimulating hormone (FSH) and estradiol. Progesterone was determined by an ELISA (Enzyme Linked Imuno-Sorbent Assay), and the levels of LH, FSH and estradiol were determined by radio-immunoassays.

When the devices were applied to the mares, a corresponding rise in LH was observed after 2 hrs., and the level of LH in serum remained higher than the baseline even after 24 hrs. The LHRH was, thus, absorbed quickly through the skin.

Table 1 below shows the serum levels of LH for each mare from day-1 to day 20 of the study period.

TABLE 1

Luteinizing Hormone (LH) Serum Levels (mIU/ml)

| Day | Mare Number | | | | | | | | | | | |
|---|---|---|---|---|---|---|---|---|---|---|---|---|
| | 1 | 2 | 3 | 4 | 5 | 7 | 8 | 9 | 10 | 11 | 12 |
| −1 | <1 | <1 | 2.2 | 4.6 | 4.6 | 3.4 | 1.7 | 5.4 | 3.8 | 2.2 | 5.0 |
| 1 | 4.1 | 7.0 | 6.5 | 7.5 | 6.1 | 10.5 | 5.3 | 8.1 | 6.6 | 6.9 | 7.4 |
| 2 | 3.8 | 6.2 | 5.5 | 6.6 | 5.5 | 4.5 | 5.7 | 7.4 | 6.2 | 6.9 | 8.7 |
| 3 | 7.7 | 4.6 | 3.4 | 5.8 | 4.1 | 4.3 | 5.1 | 5.2 | 4.2 | 4.8 | 9.3 |
| 4 | 2.4 | 3.6 | 3.1 | 3.7 | 2.6 | 3.7 | 3.5 | 4.9 | 2.4 | 3.7 | 4.9 |
| 5 | 2.9 | 3.5 | 3.1 | 4.5 | 3.5 | 3.7 | 3.8 | 4.8 | 3.0 | 4.6 | 3.9 |
| 6 | 2.5 | 2.5 | 3.4 | 4.2 | 3.4 | 2.8 | 1.0 | 3.0 | 3.8 | 4.6 | 7.7 |
| 7 | 4.8 | 3.0 | 6.2 | 5.0 | 6.8 | 7.5 | 4.4 | 7.5 | 7.5 | 6.2 | 7.5 |
| 8 | 6.2 | 4.0 | 5.4 | 7.5 | 6.8 | 8.5 | 6.8 | 7.0 | 7.5 | 8.5 | 7.5 |
| 9 | 6.8 | 6.8 | 7.0 | 8.0 | 6.2 | 9.0 | 6.8 | 7.5 | 7.0 | 7.5 | 5.4 |
| 10 | 5.4 | 6.0 | 3.6 | 8.0 | 6.8 | 5.4 | 4.4 | 7.0 | 5.0 | 5.0 | 7.5 |
| 11 | 5.4 | 5.4 | 5.4 | 6.8 | 4.8 | 6.8 | 4.0 | 7.0 | 6.2 | 8.0 | 8.5 |
| 12 | 6.2 | 7.5 | 5.0 | 8.0 | 6.8 | 6.2 | 5.4 | 8.0 | 7.0 | 7.5 | 8.5 |
| 13 | 8.5 | 7.0 | 6.8 | 7.0 | 6.2 | 6.8 | 6.2 | 8.0 | 6.0 | 7.5 | 7.5 |
| 14 | 6.2 | 6.2 | 5.0 | 8.5 | 6.0 | 7.5 | 4.4 | 7.5 | 6.8 | 7.5 | 7.5 |
| 15 | 6.2 | 6.0 | 7.0 | 8.0 | 3.4 | 7.0 | 3.8 | 6.0 | 4.4 | 4.6 | 6.0 |
| 16 | 2.2 | 4.6 | 3.4 | 5.4 | 1.7 | 3.4 | 3.8 | 4.2 | 5.0 | 5.4 | 4.4 |
| 17 | 3.8 | 4.2 | 5.0 | 7.5 | 4.2 | 4.2 | 4.2 | 7.5 | 4.4 | 4.4 | 7.0 |
| 18 | 3.4 | 4.2 | 1.4 | 5.4 | 1.7 | 4.4 | 23.0 | 6.0 | 4.4 | 6.0 | 4.4 |
| 19 | 2.5 | 2.2 | 2.5 | 6.0 | 2.9 | 5.4 | 2.9 | 4.4 | 4.6 | 8.0 | 7.5 |
| 20 | 3.4 | 2.2 | 3.4 | 7.0 | 2.9 | 4.2 | 2.2 | 4.2 | 8.5 | 3.4 | 6.0 |

The serum concentrations of FSH (mIU/ml), progesterone (ng/ml), and estradiol (pg/ml) were also obtained for mares 1 to 5 and 7 to 12 as a function of the day relative to the initiation of the electrotransport treatment.

Mares 1 to 5 and 7 to 12 were rectally examined by a veterinary surgeon to determine the stage of their estrous cycle. The rectal examinations were performed prior to the electrotransport LHRH treatment described above and on days 3, 5, 8, 10, 13, 15, 17 and 20. Table 2 shows the observations made one day prior to starting treatment.

TABLE 2

Veterinary's Observations One day prior to Treatment

| Mare | Left Ovary | Right Ovary | Cervix Size |
|---|---|---|---|
| 1 | + | 2 B–C | 3 Fingers |
| 2 | + | – | 2 Fingers |
| 3 | – | 2 B–C | 2 Fingers |
| 4 | About Ovulate | Small Inactive | Closed |
| 5 | – | 2½ B | 5 Fingers |
| 7 | ++ | 2 | 4 Fingers |
| 8 | Ovulated | Ovulated | Closed |
| 9 | Inactive | – | 2 Fingers |
| 10 | Ovulated | 2½ | 1 Finger |
| 11 | 2½ B | – | 5 Fingers Wide Open |
| 12 | 2½ | Ovulated | Closed |

Table 3 shows the observations made on day 15 after starting treatment.

TABLE 3

Veterinary's Observations Made on day 15 after Starting Treatment

| Mares | Left Ovary | Right Ovary | Cervix |
|---|---|---|---|
| 1 | L+ | 2½ B–C | 2 Fingers |
| 2 | L– | R2 | Open |
| 3 | L+ | R+ | Closed |
| 4 | L+ | R– | Closed |
| 5 | L2 C | R3 B | Open |
| 7 | Ovulated | – | Closed |
| 8 | L2 | R2 | Closed |
| 9 | Inactive | R– | 2 Fingers |
| 10 | LP 3½b | R2 C | 2 Fingers |
| 11 | L3 B | – | Open |
| 12 | L2 | R– | Closed |

From the data shown in Table 2, it appears that most, if not all, of the twelve mares were in mid-estrous cycle prior to starting the LHRH treatment regimen. By the fifth day of LHRH treatment, the majority of the animals had come into heat and had stood for the teaser. This can be deduced from the size of the animal's cervix, given that as an animal comes into estrous, its cervix dilates. At the end of the trial, all animals had come into estrous.

The blood concentrations of LH on day −1, the day prior to starting treatment, varied from about 0 to 5 mIU/ml, since the mares were at various stages of their estrous cycles. However, upon receiving the present treatment, i.e., after the initiation of LHRH electrotransport, all mares appear to have experienced the same general trend in LH concentrations in blood. A surge in LH concentration was experienced by all mares from about day 0 through day 2, which was elicited by the administration of the LHRH. Then, a decrease in LH concentration in blood occurred, with a minimum reached on day 5, the final day of administration of LHRH by electrotransport. After removal of the electrotransport device, the LH concentration in blood increased beginning on day 5, and reached a plateau on days 7 to 10. A drop in the LH serum concentration was finally observed beginning around days 14 to 15.

Having thus generally described the invention, and described in detail certain preferred embodiments thereof, it will be readily apparent that various modifications to the invention may be made by those skilled in the art, without departing from the scope of this invention, which is limited only by the following claims.

It is claimed:

1. A method of inducing ovulation in a female mammal having seasonal estrous and anestrous periods, comprising administering an agent selected from the group consisting of LHRH, prodrugs of LHRH, analogs of LHRH, salts thereof and mixtures thereof, to the mammal during a seasonal anestrous period by electrotransport through a body surface of the mammal over a period of time effective to, and in an amount sufficient to, induce ovulation in the mammal.

2. The method of claim 1, including inseminating the mammal after inducing ovulation.

3. The method of claim 1, wherein the agent is continuously delivered by electrotransport for at least about 80% of the administration period.

4. The method of claim 3, wherein the predetermined time is about 3 to 7 days after initiating the electrotransport administration of the agent.

5. A method of inducing ovulation in a female mammal having seasonal estrous and anestrous periods, comprising administering an agent selected from the group consisting of LHRH, prodrugs of LHRH, analogs of LHRH, salts thereof and mixtures thereof, to the mammal during a seasonal estrous period by electrotransport through a body surface of the mammal over a period of time effective to, and in an amount sufficient to, restart the estrous cycle of the mammal.

6. The method of claim 5, including inseminating the mammal after inducing ovulation.

7. The method of claim 1, wherein the agent is delivered at a rate of about 0.1 to 10 mg over a period of about 1 to 10 days.

8. The method of claim 7, wherein the agent is delivered at a rate of about 0.5 to 5 mg.

9. The method of claim 1, wherein the agent is continuously delivered at a rate of about 0.05 to 15 $\mu$g/hr.

10. The method of claim 9, wherein the agent is continuously delivered at a rate of about 0.5 to 10 $\mu$g/hr.

11. The method of claim 1, wherein the body surface comprises skin of the mammal.

12. The method of claim 11, including shaving the skin of the mammal before administering the LHRH.

13. The method of claim 11, wherein the skin is a skin site selected from the group consisting of an area of the underside of the mammal, the underside of the mammal between the front legs, an interior surface of a leg, and the neck of the mammal.

14. The method of claim 1, wherein the agent is administered to a mammal located in the northern hemisphere between about January 1 and March 1.

15. The method of claim 1, wherein the LHRH is delivered at a substantially constant rate during the period of time.

16. The method of claim 1, including delivering a permeation enhancer to the body surface.

17. The method of claim 1, wherein the female mammal is a mare.

18. The method of claim 5, wherein the female mammal is a mare, and the administration of the agent is initiated between about January 1 and March 1.

19. The method of claim 1, wherein the mammal is a mare and the insemination is with sperm from a thoroughbred horse.

* * * * *